US007590447B2

(12) United States Patent
Dingman et al.

(10) Patent No.: US 7,590,447 B2
(45) Date of Patent: Sep. 15, 2009

(54) PACING SYSTEM ANALYZER HAVING THREE SENSING AND PACING CHANNELS (75) Inventors: Phillip Dingman, Shoreview, MN (US); Jay Axelrod, Minneapolis, MN (US); William R. Mass, Maple Grove, MN (US); Radhakrishnan Krishnan, Shoreview, MN (US); Vladimir Kovtun, Inver Grove Heights, MN (US); Jeff Childs, Eagan, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 335 days.

(21) Appl. No.: 11/124,985

(22) Filed: May 9, 2005

(65) Prior Publication Data
US 2006/0253155 A1 Nov. 9, 2006

(51) Int. Cl.
*A61N 1/37* (2006.01)
(52) U.S. Cl. .............................. 607/10; 607/27; 607/28; 607/30
(58) Field of Classification Search ................ 607/2, 607/9, 15, 18, 27, 28, 30, 59, 10; 600/509, 600/547
See application file for complete search history.

(56) References Cited
U.S. PATENT DOCUMENTS

| | | | | |
|---|---|---|---|---|
| 5,261,411 A * | 11/1993 | Hughes | ...................... | 600/481 |
| 5,662,691 A * | 9/1997 | Behan et al. | ................... | 607/32 |
| 5,836,304 A * | 11/1998 | Kellinger et al. | ............ | 600/300 |
| 5,951,484 A * | 9/1999 | Hoium et al. | ................ | 600/515 |
| 6,148,233 A * | 11/2000 | Owen et al. | ..................... | 607/5 |
| 6,285,907 B1 * | 9/2001 | Kramer et al. | ................. | 607/9 |
| 6,477,417 B1 * | 11/2002 | Levine | ........................... | 607/9 |
| 6,597,951 B2 * | 7/2003 | Kramer et al. | ................. | 607/9 |
| 6,754,528 B2 * | 6/2004 | Bardy et al. | .................... | 607/5 |
| 2005/0137629 A1 * | 6/2005 | Dyjach et al. | .................. | 607/9 |

* cited by examiner

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

A pacing system analyzer (PSA) having three or more individually controllable sensing and pacing channels provides for testing and measurement during an operation for implanting a pacemaker having three or more sensing and pacing channels. The PSA allows control and adjustment of pacing parameters including cross-channel pacing parameters relating activities between any two of the three or more channels, such as atrioventricular and interventricular pacing delays. The PSA is also capable of, among other things, displaying real-time cardiac signals, measuring amplitude and slew rate of cardiac depolarizations, and measuring lead impedance for each of the sensing and pacing channels, as well as measuring time intervals between cardiac depolarizations in two different sensing and pacing channels. In one embodiment, the PSA includes individually controllable atrial, right ventricular (RV), and left ventricular (LV) sensing and pacing channels.

25 Claims, 10 Drawing Sheets

PACING SYSTEM ANALYZER HAVING THREE SENSING AND PACING CHANNELS

TECHNICAL FIELD

This document generally relates to cardiac rhythm management (CRM) systems and particularly, but not by way of limitation, to a pacing system analyzer (PSA) including three or more independently controlled sensing and pacing channels.

BACKGROUND

An implantable pacemaker treats cardiac arrhythmias, heart failure, and/or other cardiovascular disorders by delivering electrical energy to the heart through one or more implantable leads. Before the implantation of the implantable pacemaker, an external (non-implantable) pacing and measuring device known as a pacing system analyzer (PSA) is used to ensure adequate lead placement, maintain basic cardiac functions, and/or evaluate pacing parameters for an initial programming of the implantable pacemaker. In one example of an operation implanting a pacemaker into a patient, the patient's heart is electrically connected to the PSA through implantable sensing-pacing leads. Various pacing modes and/or parameters are evaluated to determine whether the leads are properly placed and to determine a set of suitable pacing parameters. The pacemaker is then connected to the implantable leads and subcutaneously implanted in the chest area. An external programmer is used to program the pacemaker via telemetry, using the set of suitable pacing parameters determined with the PSA.

Advances in biomedical technology have provided implantable pacemakers with increasingly sophisticated features and operational modes. As a consequence, programming an implantable CRM device has become an increasingly complicated task for healthcare professionals. A known dual-chamber PSA capable of sensing electrograms from and delivering pacing pulses to two cardiac sites may not be able to accommodate desirable tests preparing for the implantation of a tri-chamber pacemaker. While a PSA remains a useful tool during the implantation, there is a need to provide a PSA that accommodates, among other things, increased number of sensing and/or pacing sites and pacing parameters.

SUMMARY

A PSA having three or more individually controllable sensing and pacing channels provides for testing and measurement during an operation for implanting a pacemaker having three or more sensing and pacing channels. The PSA allows control and adjustment of pacing parameters including cross-channel pacing parameters relating activities between any two of the three or more channels.

In one embodiment, a PSA includes first, second, and third sensing and pacing channels, a pacing control circuit, a housing, and a user interface. The first, second, and third sensing and pacing channels each include a sensing circuit to sense a cardiac signal indicative of cardiac events and a pacing circuit to deliver pacing pulses. The pacing control circuit controls the delivery of the pacing pulses using a plurality of pacing parameters including user-programmable pacing parameters. The first, second, and third sensing and pacing channels and the pacing control circuit are enclosed in the housing. The user interface is electrically connected to the pacing control circuit and includes a pacing parameter input and a presentation device. The pacing parameter input allows programming of the user-programmable pacing parameters. The presentation device includes a display screen that displays the first, second, and third cardiac signals in real time.

In one specific embodiment, the first sensing and pacing channel is an atrial sensing and pacing channel, the second sensing and pacing channel is a right ventricular (RV) sensing and pacing channel, and the third sensing and pacing channel is a left ventricular (LV) sensing and pacing channel. The pacing parameter input allows programming of an interventricular delay being an offset interval between a delivery of one of the RV pacing pulses and a delivery of one of the LV pacing pulses.

In one embodiment, a method for operating a PSA is provided. Cardiac signals indicative of cardiac events are sensed using three sensing and pacing channels of the PSA. A predetermined pacing algorithm is executed to control a delivery of pacing pulses using a plurality of pacing parameters including user-programmable pacing parameters. The pacing pulses are delivered using the three sensing and pacing channels. Lead impedance values each associated with one of sensing and pacing channels are measured. Event parameters each associated with one of the cardiac events are measured. Conduction intervals are measured as a time interval between two cardiac events selected from two of the first, second, and third cardiac events.

In a specific embodiment, the cardiac signals include an atrial electrogram, a right ventricular (RV) electrogram, and a left ventricular (LV) electrogram. The pacing pulses include atrial pacing pulses, the RV pacing pulses, and LV pacing pulses. Conduction intervals are measured between two depolarizations selected from two of the atrial depolarizations, the RV depolarizations, and LV depolarizations.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

In the drawings, which are for illustrative purposes only and not necessarily drawn to scale, like numerals describe similar components throughout the several views. The drawings illustrate generally, by way of example, but not by way of limitation, various embodiments of the present subject matter.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this document are not necessarily to the same embodiment, and such references contemplate more than one embodiment.

This document discusses, among other things, a PSA that includes three or more individually controlled sensing and pacing channels. The PSA provides for testing during an operation for implanting a pacemaker having three or more sensing and pacing channels, such as a biventricular pacemaker having atrial, RV, and LV channels. The PSA allows control and adjustment of pacing parameters including cross-channel pacing parameters such as atrioventricular and interventricular pacing delays. The PSA is also capable of displaying real-time electrograms, displaying event markers, performing measurements in each individual sensing and pacing channel, and performing cross-channel measurements. Examples of the measurements in each individual sensing and pacing channel include measurement of amplitude and slew rate associated with cardiac depolarizations and measurement of lead impedance associated with each sensing and pacing channel. Examples of the cross-channel measurements include measurements of time intervals between cardiac depolarizations in two different sensing and pacing channels, such as an atrioventricular interval and an interventricular interval.

Figure 1:
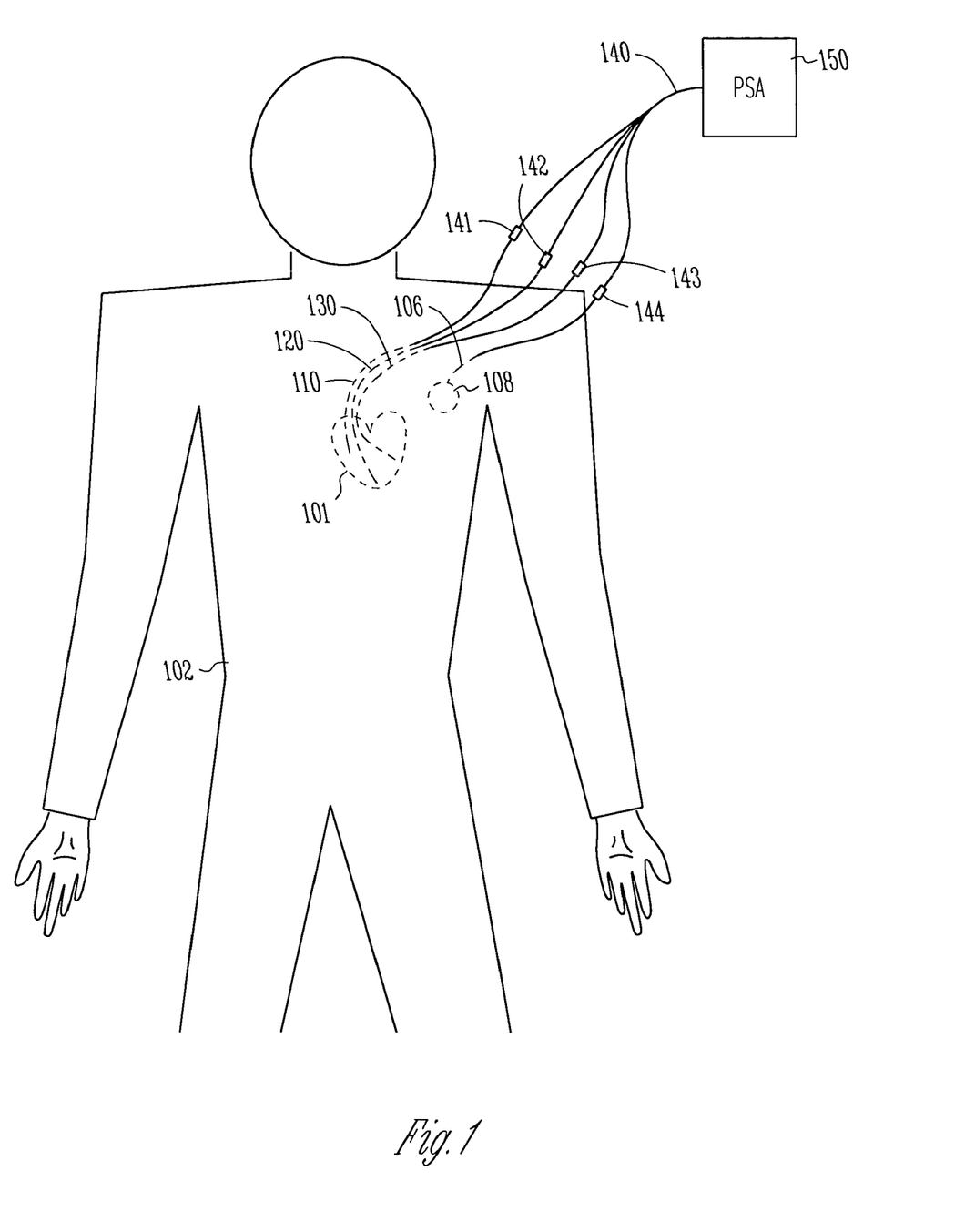
FIG. 1 is an illustration of an embodiment of a PSA and portions of the environment in which the PSA is used.

FIG. 1 is an illustration of an embodiment of a PSA 150 and portions of the environment in which PSA 150 is used. Before implantation of an implantable pacemaker into a body 102, portions of pacing leads 110, 120, and 130 are inserted into a heart 101. These pacing leads each include one or more electrodes for placement in or on heart 101 for sensing electrograms and delivering pacing pulses. Another lead 106 is connected to a reference electrode 108, which is also used for sensing electrograms and delivering pacing pulses. The electrodes of leads 110, 120, and 130 and electrode 108 are electrically connected to PSA 150 using a cable 140 with connectors 141, 142, 143, and 144. Connectors 141, 142, 143, and 144 are each configured for a temporary connection between cable 140 to one of leads 110, 120, 130, and 106. PSA 150 performs a test including pacing and measurements to ensure that leads 110, 120, and 130 are properly positioned and to find a set of suitable pacing parameters. When the test is completed, cable 140 is disconnected from the leads, and lead 106 (with reference electrode 108) is removed from body 102. An implantable pacemaker is connected to leads 110, 120, and 130 and is implanted in body 102 in approximately the location where electrode 108 was placed. The set of pacing parameters determined during the test is programmed into the implantable pacemaker as the initial pacing parameters with which a pacing therapy starts. The implantable pacemaker has a housing that includes a conductive portion used as a reference electrode, replacing electrode 108.

PSA 150 includes at least three individually controllable sensing and pacing channels. In an embodiment, as illustrated in FIG. 1, PSA 150 includes three individually controllable sensing and pacing channels to provide for sensing of atrial, RV, and/or LV electrograms and delivery of atrial, RV, and/or LV pacing pulses. In a specific application, PSA 150 allows for pacing system testing before implantation of a cardiac resynchronization therapy (CRT) device having atrial, RV, and LV channels. During the testing, PSA 150 performs various measurements and executes a CRT pacing algorithm using programmable pacing parameters including, but not limited to, atrioventricular and interventricular pacing delays. In another embodiment, PSA 150 includes four individually controllable sensing and pacing channels. In a specific application, a four-channel PSA 150 allows for pacing system testing before implantation of a cardiac resynchronization therapy (CRT) device having atrial, RV, and two LV channels.

Figure 2:
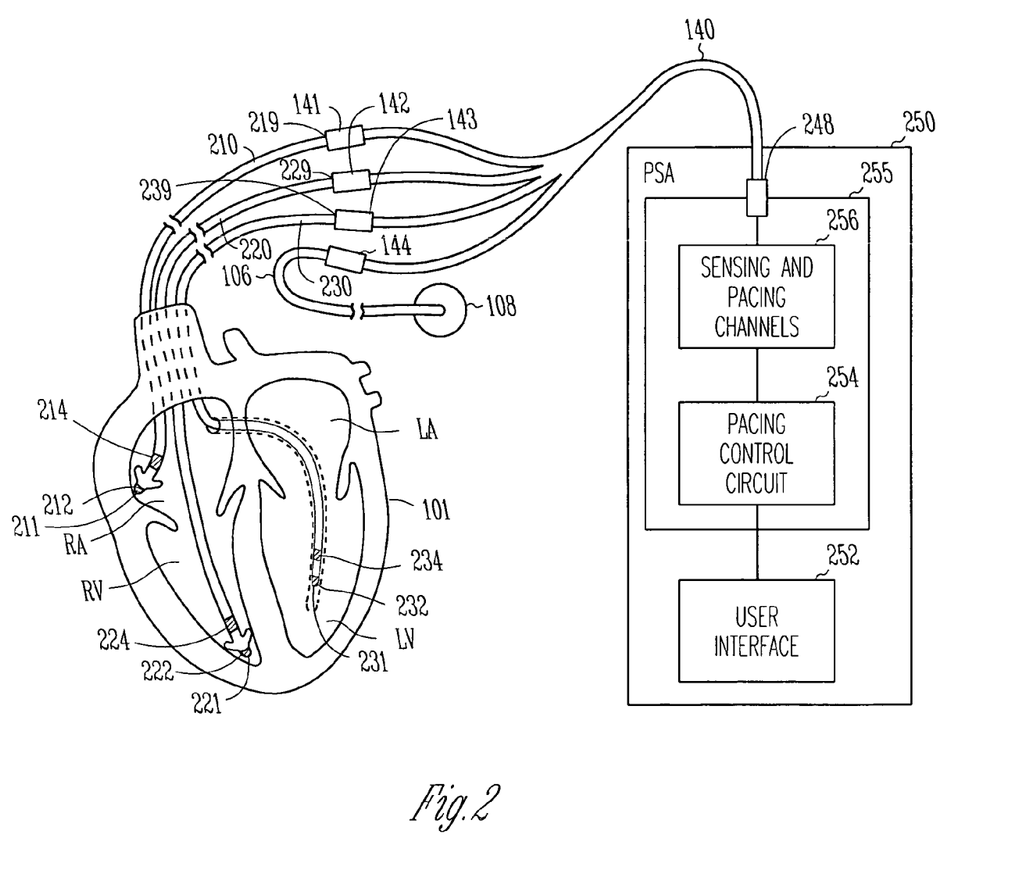
FIG. 2 is an illustration of an exemplary embodiment of sensing and pacing electrodes coupled to the PSA.

FIG. 2 is an illustration of an exemplary embodiment of sensing and pacing electrodes coupled to PSA 250. Lead 210 is a specific embodiment of lead 110. Lead 220 is a specific embodiment of lead 120. Lead 230 is a specific embodiment of lead 130. PSA 250 is a specific embodiment of PSA 150.

As illustrated in FIG. 2, lead 210 is an atrial pacing lead that includes an elongate lead body having a proximal end 219 and a distal end 211. Proximal end 219 is to be coupled to connector 141 of cable 140 for connecting to PSA 250. Distal end 211 is configured for placement in the right atrium (RA). Lead 210 includes a tip electrode 212 and a ring electrode 214. Electrodes 212 and 214 are sensing-pacing electrodes incorporated into the lead body at or near distal end 211 and are each electrically coupled to a conductor extending within the lead body. Electrodes 212 and/or 214 allow for sensing an atrial electrogram indicative of depolarizations in the RA and delivering pacing pulses to the RA.

Lead 220 is an RV sensing-pacing lead including an elongate lead body having a proximal end 229 and a distal end 221. Proximal end 229 is to be coupled to connector 142 of cable 140 for connecting to PSA 250. Distal end 221 is configured for placement in the RV. Lead 220 includes a tip electrode 222 and a ring electrode 224. Electrodes 222 and 224 are sensing-pacing electrodes incorporated into the lead body at or near distal end 221 and are each electrically coupled to a conductor extending within the lead body. Electrodes 222 and/or 224 allow for sensing an RV electrogram indicative of depolarizations in the RV and delivering pacing pulses to the RV.

Lead 230 is a coronary LV sensing-pacing lead including elongate lead body having a proximal end 239 and a distal end 231. Proximal end 239 is to be coupled to connector 143 of cable 140 for connecting to PSA 250. Distal end 231 is configured for placement in the coronary vein over the LV. Lead 230 includes a tip electrode 232 and a ring electrode 234. Electrodes 232 and 234 are sensing-pacing electrodes incorporated into the lead body at or near distal end 231 and are each electrically coupled to a conductor extending within the lead body. Electrodes 232 and/or 234 allow for sensing an LV electrogram indicative of depolarizations in the LV and delivering pacing pulses to the LV.

In the exemplary embodiment illustrated in FIG. 2, sensing-pacing electrodes 212, 214, 222, 224, 232, and 234 each allow for sensing by pairing with another sensing-pacing electrode or reference electrode 108. In one embodiment, PSA 250 allows programming of various assignments of electrode pairs for electrogram sensing and/or pacing pulse delivery purposes. For example, bipolar electrode configuration is programmable for electrogram sensing and pacing pulse delivery using electrode pair 212/214, electrode pair 222/224, and/or electrode pair 232/234. Unipolar electrode configuration is programmable for electrogram sensing and pacing pulse delivery using electrode pair 212/108, electrode pair 222/108, and/or electrode pair 232/108. In one embodiment, PSA 250 also allows for electrogram sensing and pacing pulse delivery using a pair of electrodes selected from electrodes in different leads.

The leads and electrodes are illustrated in FIG. 2 by way of example but not by way of limitation. After reading and comprehending this document, those skilled in the art will understand that the PSA discussed herein accommodates up to three or more leads each including one or more electrodes that are used with an implantable pacemaker.

PSA 250 has a housing 255 enclosing electronic circuitry including sensing and pacing channels 256 and a pacing control circuit 254. Sensing and pacing channels 256 include three or more individually controllable sensing and pacing circuits for sensing from and delivering pacing pulses to three or more cardiac sites. Pacing control circuit 254 controls the overall operation of PSA 250, including the delivery of the pacing pulses in each sensing and pacing channel. PSA 250 also includes a user interface 252, which is electrically connected to the electronic circuitry enclosed in housing 255. User interface 252 allows a user such as a physician or other caregiver to operate PSA 250 and observe information acquired by PSA 250. In one embodiment, user interface 252 is mounted on housing 255. In another embodiment, user interface 252 is electrically connected to the electronic circuitry enclosed in housing 255 using wires or a cable. In one embodiment, the user interface of a computer or a computer-based medical device programmer is used as user interface 252. PSA 250 is electrically connected to the computer or computer-based medical device programmer. In a specific embodiment, PSA 250 is incorporated into the computer or computer-based medical device programmer. In another specific embodiment, PSA 250 is configured for detachable attachment to the computer or computer-based medical device programmer. Housing 255 is configured for insertion or attachment to the computer or computer-based medical device programmer, and a standard interface such as a USB cable is used to electrically connect PSA 250 to the computer or a computer-based medical device programmer. A cable connector 248 is mounted on housing 255 to provide an interface between cable 140 and PSA 250. In one embodiment, cable connector 248 provides for a detachable connection, and cable 140 can be detached from PSA 250 when not in use. Embodiments of the circuit of PSA 250 are discussed below with reference to FIGS. 3-7.

Figure 3:
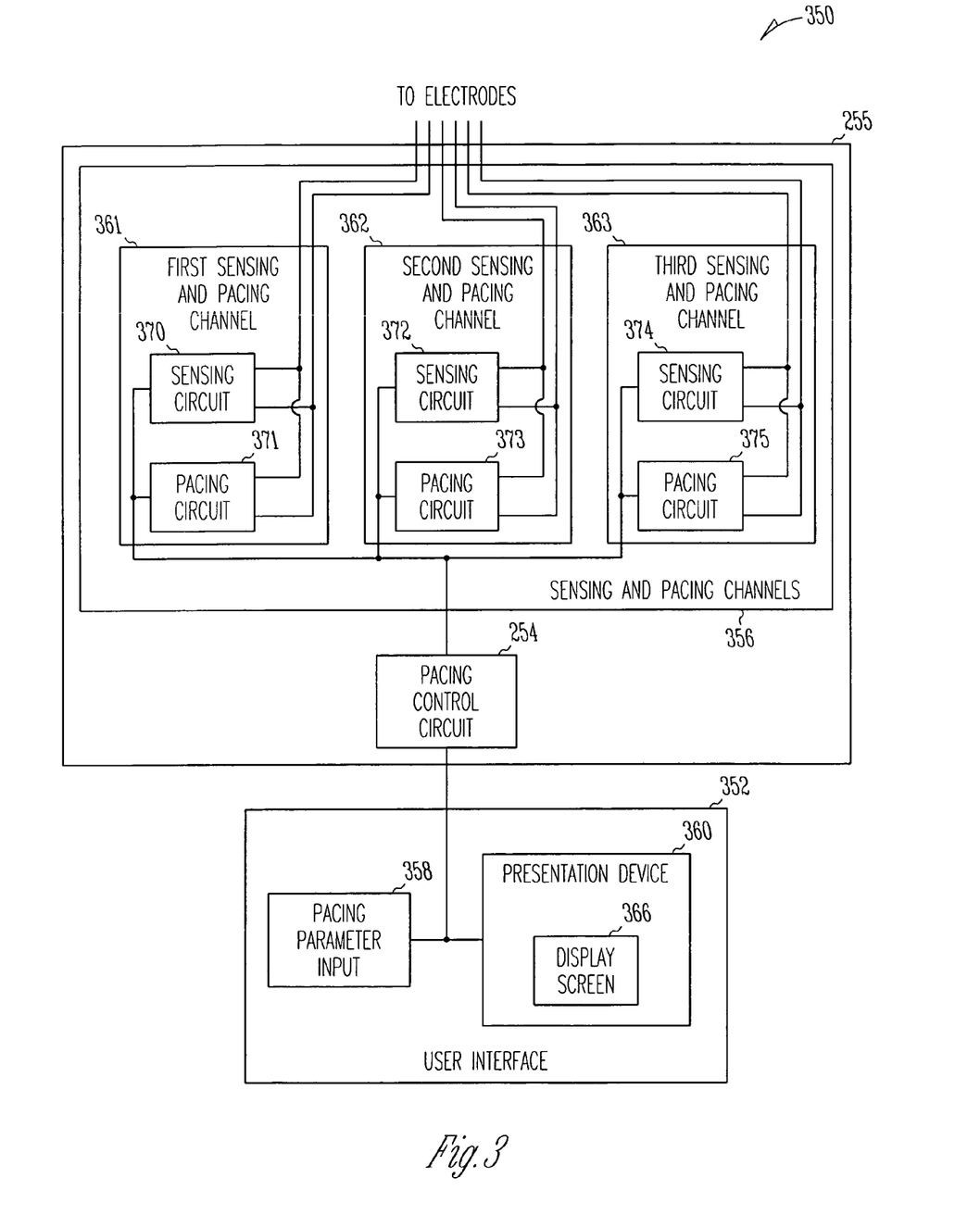
FIG. 3 is a block diagram illustrating an embodiment of a circuit of the PSA.

FIG. 3 is a block diagram illustrating an embodiment of a PSA circuit 350, which is an embodiment of a circuit of PSA 250. PSA circuit 350 includes sensing and pacing channels 356, pacing control circuit 254, and a user interface 352. Sensing and pacing channels 356 and pacing control circuit 254 are enclosed in housing 255. User interface 352 is electrically connected to the circuitry enclosed in housing 255.

As illustrated in FIG. 3, sensing and pacing channels 356 include a first sensing and pacing channel 361, a second sensing and pacing channel 362, and a third sensing and pacing channel 363. First sensing and pacing channel 361 includes a sensing circuit 370 to sense a first cardiac signal indicative of cardiac events occurring in a first cardiac region and a pacing circuit 371 to deliver pacing pulses to the first cardiac region. Second sensing and pacing channel 362 includes a sensing circuit 372 to sense a second cardiac signal indicative of cardiac events occurring in a second cardiac region and a pacing circuit 373 to deliver pacing pulses to the second cardiac region. Third sensing and pacing channel 363 includes a sensing circuit 374 to sense a third cardiac signal indicative of cardiac events occurring in a third cardiac region and a pacing circuit 375 to deliver pacing pulses to the third cardiac region. In one embodiment, the first, second, and third cardiac regions are within three different cardiac chambers. In another embodiment, two or more of the first, second, and third cardiac regions are within one cardiac chamber.

Pacing control circuit 254 controls the delivery of pacing pulses to the first, second, and/or third cardiac regions using a plurality of pacing parameters including user-programmable pacing parameters. PSA 250 allows for evaluation of the user-programmable pacing parameters.

User interface 352 is a specific embodiment of user interface 252 and includes a pacing parameter input 358 and a presentation device 360. Pacing parameter input 358 allows the user to enter and/or adjust the user-programmable pacing parameters. Presentation device 360 includes a display screen 366 for displaying the first, second, and third cardiac signals in real time.

Figure 4:
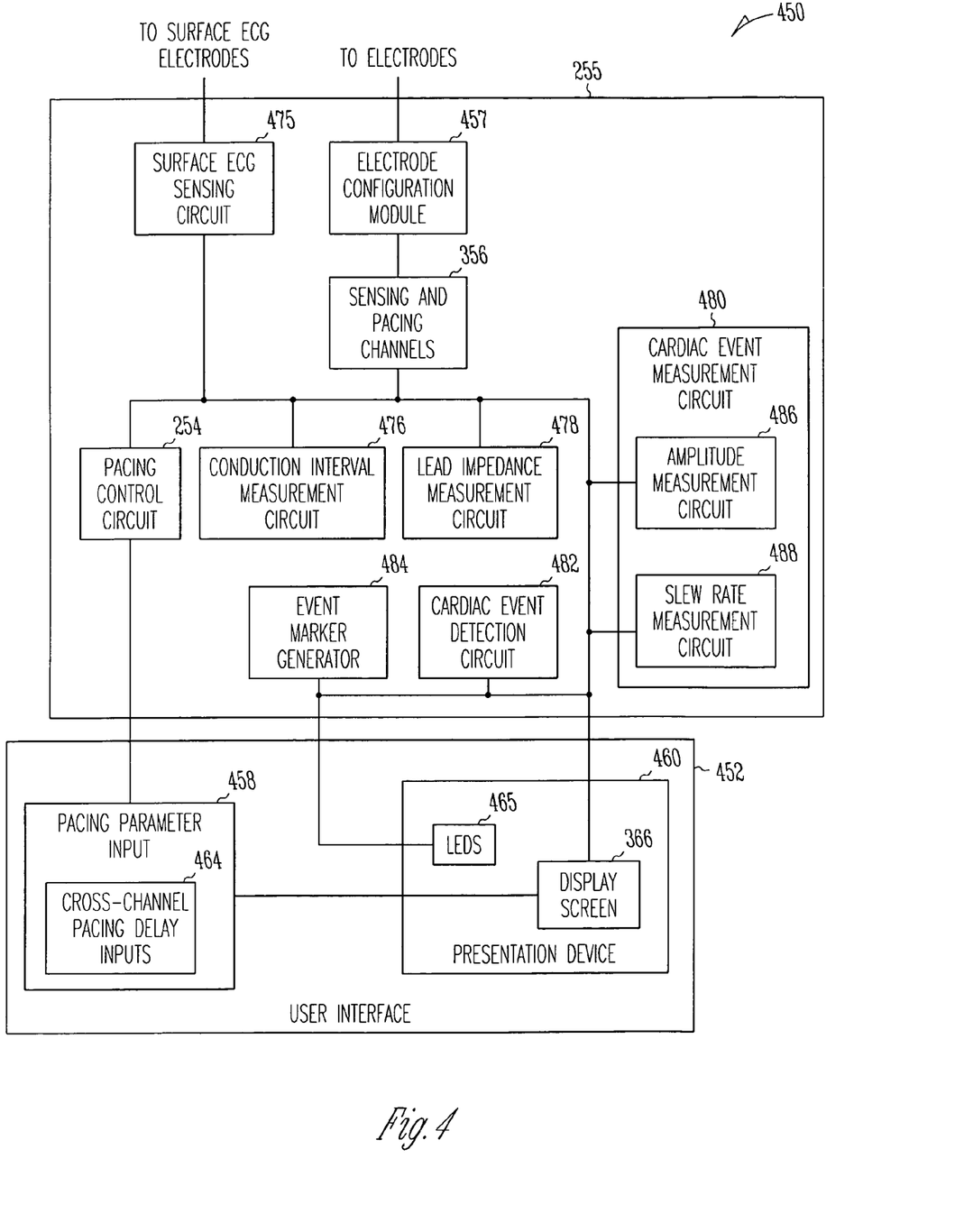
FIG. 4 is a block diagram illustrating a specific embodiment of the circuit of the PSA.

FIG. 4 is a block diagram illustrating an embodiment of a PSA circuit 450, which is a specific embodiment of PSA circuit 350. PSA circuit 450 includes sensing and pacing channels 356, an electrode configuration module 457, pacing control circuit 254, a conduction interval measurement circuit 476, a lead impedance measurement circuit 478, a cardiac event measurement circuit 480, a cardiac event detection circuit 482, an event marker generator 484, and a user interface 452. Sensing and pacing channels 356, electrode configuration module 457, pacing control circuit 254, conduction interval measurement circuit 476, lead impedance measurement circuit 478, cardiac event measurement circuit 480, cardiac event detection circuit 482, and event marker generator 484 are enclosed in housing 255, User interface 452 is electrically connected to the circuitry enclosed in housing 255. In one embodiment, as illustrated in FIG. 4, PSA 450 further includes a surface ECG sensing circuit 475 to sense one or more surface ECG signals through surface ECG electrodes attached to the skin. In the embodiment illustrated in FIG. 4, surface ECG sensing circuit 475 is enclosed in housing 255. In another embodiment, surface ECG sensing circuit 475 is external to in housing 255 but electrically connected to the circuitry enclosed in housing 255.

Electrode configuration module 457 includes switches that provide for programmable connections between electrodes (such as those selected from electrodes 212, 214, 222, 224, 232, 234, and 108) and sensing and pacing channels 356. In one embodiment, electrode configuration module 457 allows the connections to be made for predetermined bipolar and/or unipolar electrode configurations. In another application, electrode configuration module 457 allows the connections each to be made between any two electrodes selected from electrodes placed in the body.

Pacing control circuit 254 controls the delivery of the pacing pulses by executing a predetermined pacing algorithm using the plurality of pacing parameters including the user-programmable pacing parameters. In one embodiment, pacing control circuit 254 includes a pacing parameter storage circuit that receives and stores values of the plurality of pacing parameters. The user-programmable pacing parameters include, among other things, cross-channel pacing delay for delivering a pacing pulse to a cardiac region after a predetermined delay interval starting with a cardiac event sensed from or a pacing pulse delivered to another cardiac region.

Conduction interval measurement circuit 476 measures one or more conduction intervals each being a time interval between two cardiac events. The conduction intervals include cross-channel conduction intervals each being a time interval between a cardiac event sensed in one cardiac region and another cardiac event sensed in another cardiac region. In one embodiment, conduction interval measurement circuit 476 includes at least two of first, second, and third conduction interval measurement circuits. The first conduction interval measurement circuit measures a first conduction interval being a time interval between a cardiac event in the first cardiac region and a successive cardiac event in the second cardiac region. The second conduction interval measurement circuit measures a second conduction interval being a time interval between a cardiac event in the first cardiac region and a successive cardiac event in the third cardiac region. The third conduction interval measurement circuit measures a third conduction interval being a time interval between a cardiac event in the second region and a successive cardiac event in the third cardiac region. In one embodiment, conduction interval measurement circuit 476 includes a continuous conduction interval measurement circuit to measure one or more conduction intervals on a beat-by-beat basis. In another embodiment, conduction interval measurement circuit 476 includes a periodic conduction interval measurement circuit to measure one or more conduction intervals on a periodic basis. In another embodiment, conduction interval measurement circuit 476 measures one or more conduction intervals upon request received from the user.

Lead impedance measurement circuit 478 measures lead impedance values each associated with one of the leads coupled to sensing and pacing channels 356. A lead impedance value associated with a lead is calculated based on the voltage of a pacing pulse delivered through that lead and the current produced by the pacing pulse and flowing in the lead. In one embodiment, lead impedance measurement circuit 478 includes a continuous impedance measurement circuit to measure the lead impedance values on a continuous basis while the predetermined pacing algorithm is being executed. That is, after each delivery of a pacing pulse through a lead, the continuous impedance measurement circuit measures the impedance associated with that lead. In another embodiment, lead impedance measurement circuit 478 includes a periodic impedance measurement circuit to measure the lead impedance values on a periodic basis. In another embodiment, lead impedance measurement circuit 478 measure one or more lead impedance values upon request received from the user.

Cardiac event measurement circuit 480 measures one or more event parameters each associated with one of the cardiac events occurring in the first, second, and third cardiac regions. In one embodiment, cardiac event measurement circuit 480 includes an amplitude measurement circuit 486 and a slew rate measurement circuit 488. Amplitude measurement circuit 486 measures one or more amplitudes each associated with one of the cardiac events occurring in the first, second, and third cardiac regions. Slew rate measurement circuit 488 measures one or more slew rates each associated with one of the cardiac events occurring in the first, second, and third cardiac regions. In one embodiment, cardiac event measurement circuit 480 includes a continuous cardiac event measurement circuit to measure one or more event parameters on a beat-by-beat basis. In another embodiment, cardiac event measurement circuit 480 includes a periodic cardiac event measurement circuit to measure the one or more event parameters on a periodic basis. In another embodiment, cardiac event measurement circuit 480 measure one or more event parameters upon request received from the user.

In one embodiment, conduction interval measurement circuit 476, lead impedance measurement circuit 478, and cardiac event measurement circuit 480 are capable of concurrently measuring conduction intervals, lead impedance values, and event parameters associated with all the sensing and pacing channels.

Cardiac event detection circuit 482 detects the cardiac events occurring in the first, second, and third cardiac regions. Event marker generator 484 produces sense markers each indicative of a detection of a cardiac event from one of the first, second, and third cardiac regions and pace markers each indicative of the delivery of a pacing pulse to one of the first, second, and third cardiac regions.

User interface 452 includes a pacing parameter input 458 and a presentation device 460. Pacing parameter input 458 allows programming of the user-programmable pacing parameters and includes cross-channel pacing delay inputs 464. In one embodiment, cross-channel pacing delay inputs 464 includes at least two of first, second, and third cross-channel pacing delay inputs. The first cross-channel pacing delay is a pacing delay interval between the first sensing and pacing channel and the second sensing and pacing channel. The second cross-channel pacing delay is a pacing delay interval between the first sensing and pacing channel and the third sensing and pacing channel. The third cross-channel pacing delay is a pacing delay interval between the second sensing and pacing channel and the third sensing and pacing channel. Presentation device 460 includes display screen 366 and light-emitting diodes (LEDs) 465. Display screen 366 displays the first, second, and third cardiac signals in real time. In one embodiment, display screen 366 also displays the event markers along with the cardiac signals. In one embodiment, display screen 366 further displays measurement results selected from the one or more conduction intervals, the lead impedance values, the one or more event parameters, and the one or more surface ECG signals, in addition to the cardiac signals and event makers. In a specific embodiment, display screen 366 further displays the measurement results as measurement markers each associated with a cardiac event. That is, if a measurement is related to a cardiac event and is made following the detection of that cardiac event, display screen 366 displays the result of the measurement as a measurement marker temporally aligned with the cardiac event. LEDs 465 are each driven by one type of events. In one embodiment, LEDs 465 include three sense LEDs that correspond to sense markers each indicative of a detection of a cardiac event from one of the first, second, and third cardiac regions and three pace LEDs that correspond to pace markers each indicative of the delivery of a pacing pulse to one of the first, second, and third cardiac regions.

Figure 5:
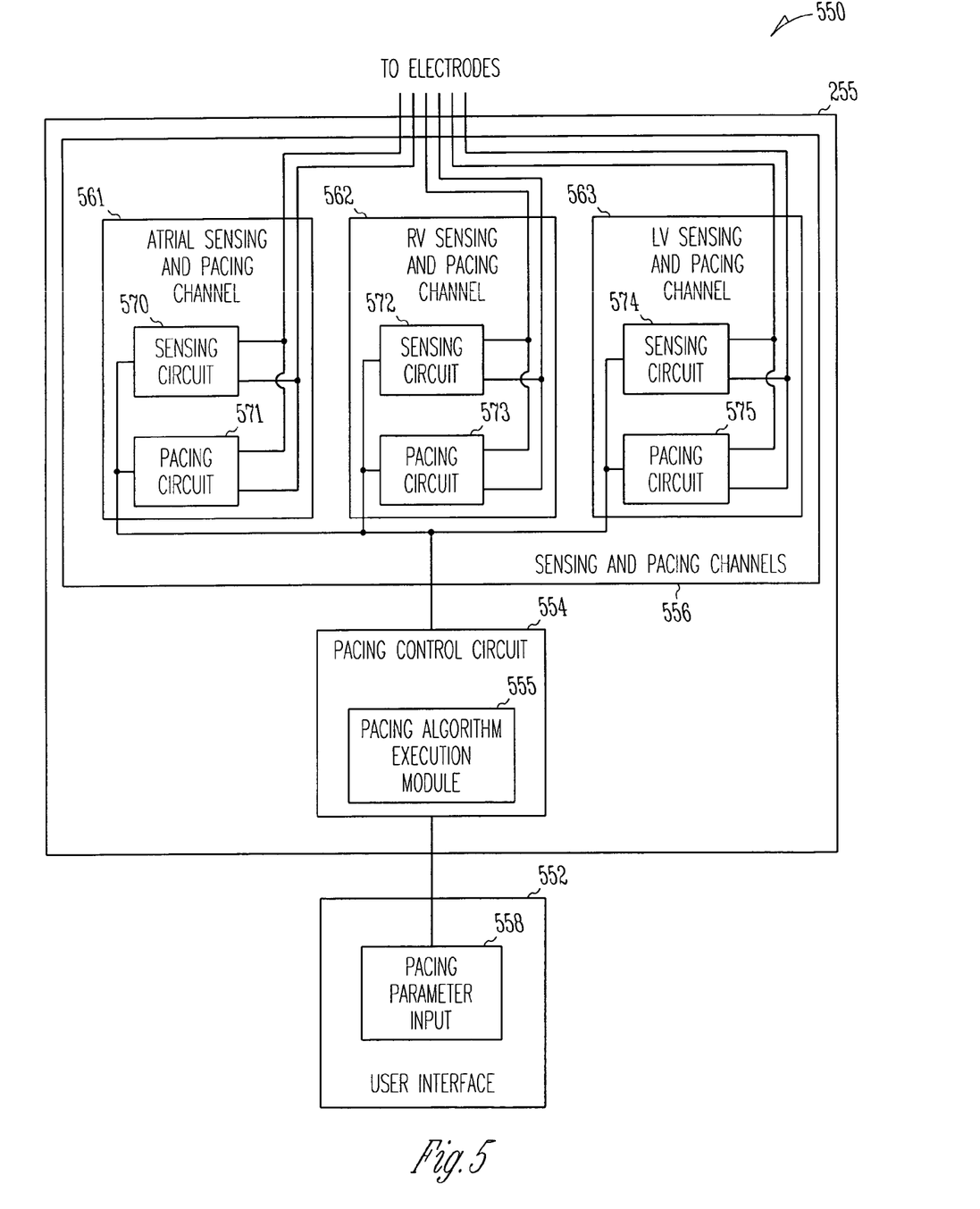
FIG. 5 is a block diagram illustrating an embodiment of a circuit of a PSA having atrial, right ventricular (RV), and left ventricular (LV) sensing and pacing channels.

FIG. 5 is a block diagram illustrating an embodiment of a PSA circuit 550. PSA circuit 550 is a specific embodiment of PSA circuit 350 for testing in preparation of implanting a biventricular pacemaker having atrial, RV, and LV sensing and pacing channels. PSA circuit 550 includes sensing and pacing channels 556, a pacing control circuit 554, and a user interface 552. Sensing and pacing channels 556 and pacing control circuit 554 are enclosed in housing 255. User interface 552 is electrically connected to the circuitry enclosed in housing 255.

Sensing and pacing channels 556 are a specific embodiment of sensing and pacing channels 356 and include three sensing and pacing channels. An atrial sensing and pacing channel 561 includes a sensing circuit 570 to sense an atrial electrogram indicative of atrial depolarizations (P-waves) and a pacing circuit 571 to deliver atrial pacing pulses. An RV sensing and pacing channel 562 includes a sensing circuit 572 to sense an RV electrogram indicative of RV depolarizations (RV R-waves) and a pacing circuit 573 to deliver RV pacing pulses. An LV sensing and pacing channel 563 includes a sensing circuit 574 to sense an LV electrogram indicative of LV depolarizations (LV R-waves) and a pacing circuit 575 to deliver LV pacing pulses. Sensing and pacing channels 556 are to be connected to electrodes such as those selected from electrodes 212, 214, 222, 224, 232, 234, and 108. In one embodiment, the connections between the electrodes and sensing and pacing channels 556 are programmable, such as by using electrode configuration module 457 discussed above.

Pacing control circuit 554 controls pacing circuits 571, 573, and 575 using a plurality of pacing parameters including user-programmable pacing parameters. Pacing control circuit 554 includes a pacing algorithm execution module 555 to control the delivery of atrial, RV and/or LV pacing pulses by executing a predetermined biventricular pacing algorithm.

User interface 552 includes a pacing parameter input 558 that allows for entry and/or adjustment of the user-programmable pacing parameters. In one embodiment, pacing parameter input 558 allows for programming of an interventricular delay being an offset interval between the delivery of an RV pacing pulse and the delivery of an LV pacing pulse during the same cardiac cycle.

Figure 6:
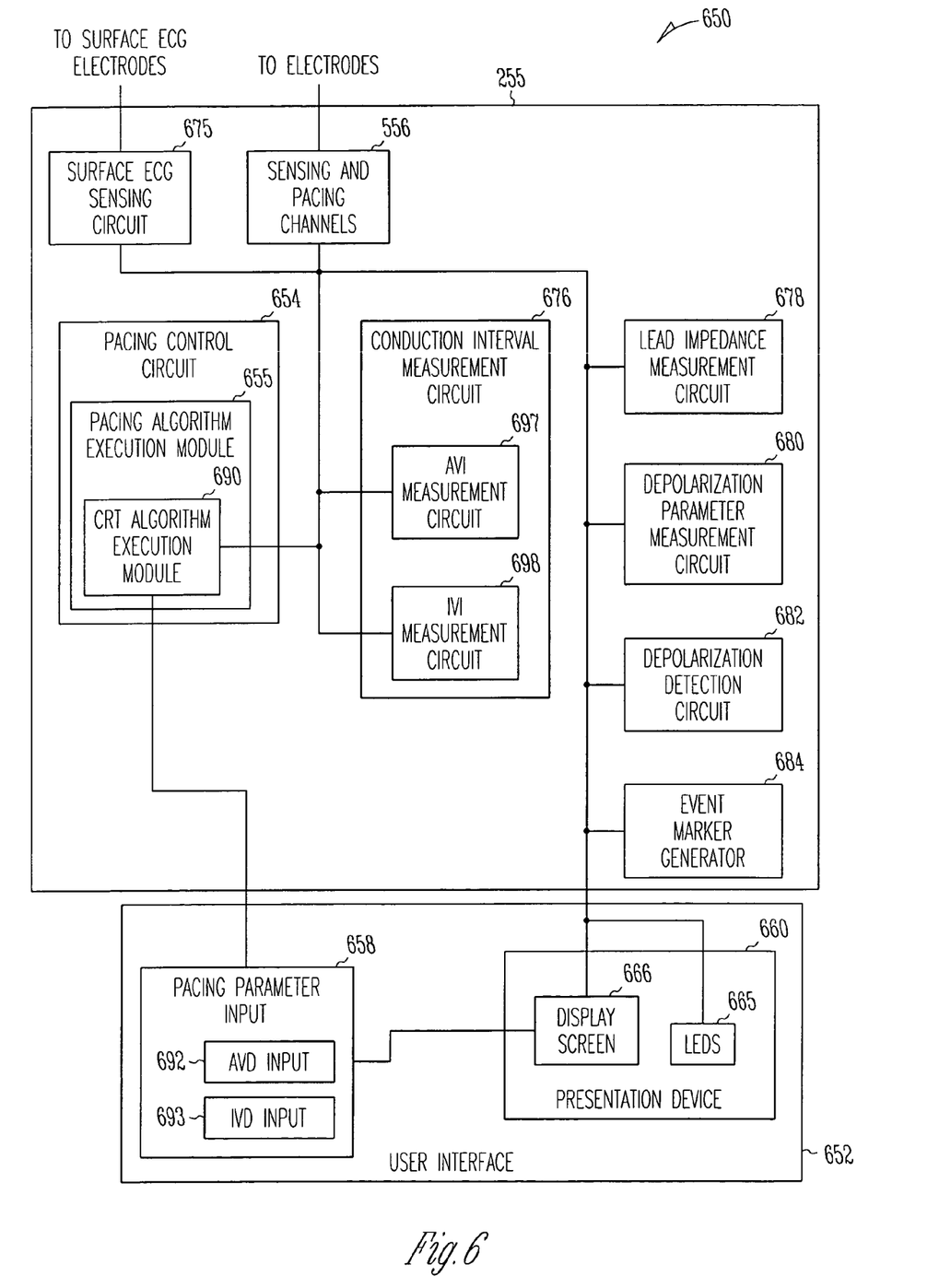
FIG. 6 is a block diagram illustrating a specific embodiment of the circuit of the PSA having the atrial, RV, and LV sensing and pacing channels.

FIG. 6 is a block diagram illustrating one embodiment of a PSA circuit 650, which is a specific embodiment of PSA circuit 550. PSA circuit 650 includes sensing and pacing channels 556, a pacing control circuit 654, a conduction interval measurement circuit 676, a lead impedance measurement circuit 678, a depolarization parameter measurement circuit 680, a depolarization detection circuit 682, an event marker generator 684, and a user interface 652. Sensing and pacing channels 556, pacing control circuit 654, conduction interval measurement circuit 676, lead impedance measurement circuit 678, depolarization parameter measurement circuit 680, depolarization detection circuit 682, and event marker generator 684 are enclosed in housing 255. User interface 652 is electrically connected to the circuitry enclosed in housing 255. In one embodiment, as illustrated in FIG. 6, PSA 650 further includes a surface ECG sensing circuit 675 to sense one or more surface ECG signals through surface ECG electrodes attached to the skin. In the embodiment illustrated in FIG. 6, surface ECG sensing circuit 675 is enclosed in housing 255. In another embodiment, surface ECG sensing circuit 675 is external to in housing 255 but electrically connected to the circuitry enclosed in housing 255.

Pacing control circuit 654 is a specific embodiment of pacing control circuit 554 and includes a pacing algorithm execution module 655. Pacing algorithm execution module 655 controls the delivery of one the atrial, RV, and/or LV pacing pulses by executing a predetermined pacing algorithm. In one embodiment, pacing algorithm execution module 655 includes a cardiac resynchronization therapy (CRT) algorithm execution module 690 to deliver a pacing therapy treating heart failure by executing a CRT pacing algorithm. Pacing algorithm execution module 655 includes a pacing parameter storage circuit to receive and store values of a plurality of programmable pacing parameters used by the predetermined pacing algorithm. The pacing parameter storage circuit includes a cross-channel pacing delay parameter circuit to receive and store an atrioventricular delay (AVD) for timing the delivery of an RV or LV pacing pulse after an atrial depolarization and an interventricular delay (IVD) for timing an offset interval between the delivery of an RV pacing pulse and the delivery of an LV pacing pulse.

Conduction interval measurement circuit 676 includes an atrioventricular interval (AVI) measurement circuit 697 and an interventricular interval (IVI) measurement circuit 698. AVI measurement circuit 697 measures an AVI being a time interval between an atrial depolarization and a successive RV depolarization and/or an AVI being a time interval between the atrial depolarization and a successive LV depolarization. IVI measurement circuit 698 measures an IVI being a time interval between an RV depolarization and a successive LV depolarization. Lead impedance measurement circuit 678 measures lead impedance values each associated with one channel of sensing and pacing channels 556. Depolarization parameter measurement circuit 680 measures depolarization parameters each associated with an atrial, RV, or LV depolarization. Examples of the depolarization parameters include amplitudes and slew rates each associated with an atrial, RV, or LV depolarization. Depolarization detection circuit 682 detects the atrial depolarizations, RV depolarizations, and LV depolarizations. Event marker generator 684 produces sense markers each indicative of the detection of an atrial, RV, or LV depolarization and pace markers each indicative of the delivery of an atrial, RV, or LV pacing pulse.

User interface 652 includes a pacing parameter input 658 and a presentation device 660. Pacing parameter input 658 allows programming of the user-programmable pacing parameters used in the execution of the predetermined pacing algorithm. Pacing parameter input 658 includes, among other inputs, an AVD input 692 to allow entry and/or adjustment of the value of at least one AVD and an IVD input 693 to allow entry or adjustment of the value of the IVD. Presentation device 660 includes a display screen 666 and LEDs 665. Display screen 666 displays the atrial, RV, and LV electrograms in real time. In one embodiment, display screen 666 also displays the sense and pace markers along with the atrial, RV, and LV electrograms. In one embodiment, display screen 666 further displays measurement results selected from the AVIs, the IVI, the lead impedance values, the depolarization parameters, and the one or more surface ECG signals, in addition to the atrial, RV, and LV electrograms and the sense and pace makers. In a specific embodiment, display screen 666 further displays the measurement results as measurement markers each associated with a cardiac event. That is, if a measurement is related to a cardiac event and is made following the detection of that cardiac event, display screen 666 displays the result of the measurement as a measurement marker temporally aligned with the cardiac event. For example, if an atrial lead impedance is made following the delivery of an atrial pacing pulse, display screen 666 displays the impedance value temporally aligned with the atrial pacing pulse as seen on the atrial electrogram, such as the impedance value is visually perceived as associated with that atrial pacing pulse. The visual presentation of the electrograms, sense and pace markers, and measurement markers on display screen 666 is further discussed below, with reference to FIG. 10. LEDs 665 include sense LEDs and pace LEDs. The sense LEDs include an atrial sense LED driven by the atrial sense markers, an RV sense LED driven by the RV sense markers, and an LV sense LED driven by the LV sense markers. The pace LEDs includes an atrial pace LED driven by the atrial pace markers, an RV pace LED driven by the RV pace markers, and an LV pace LED driven by the LV pace markers.

Figure 7:
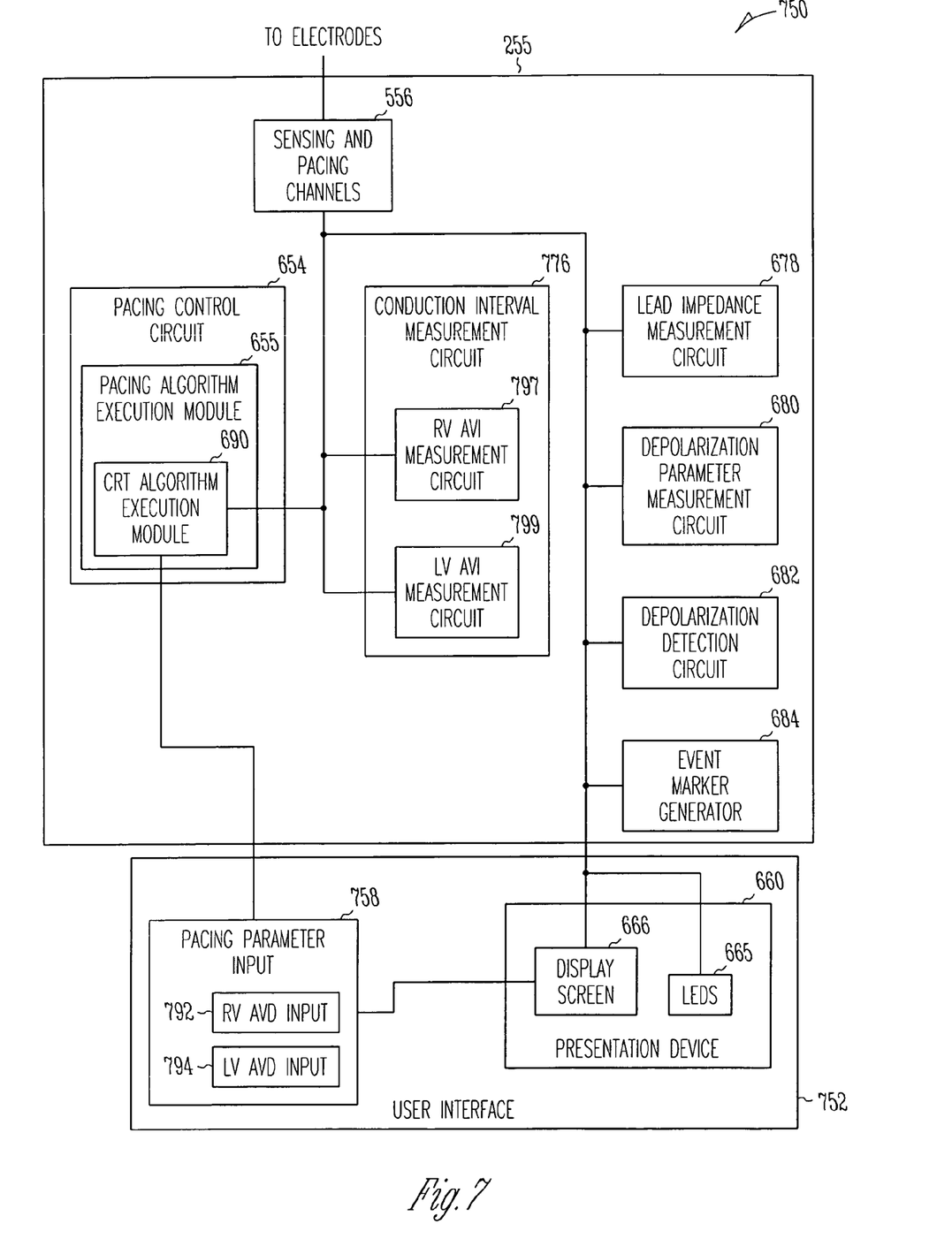
FIG. 7 is a block diagram illustrating another specific embodiment of the circuit of the PSA having the atrial, RV, and LV sensing and pacing channels.

FIG. 7 is a block diagram illustrating one embodiment of a PSA circuit 750, which is another specific embodiment of PSA circuit 550. PSA circuit 750 is an alternative embodiment of PSA circuit 650 with conduction interval measurement circuit 676 replaced by a conduction interval measurement circuit 776 and user interface 652 replaced by a user interface 752. Because the IVI is essentially the difference between an AVI measured with an RV depolarization and another AVI measured with an LV depolarization, and the IVD is essentially the difference between an AVD for the RV and another AVD for the LV, PSA circuit 750 measures only AVIs and controls only AVDs. Accordingly, conduction interval measurement circuit 776 includes an RV AVI measurement circuit 797 to measure an RV AVI being the time interval between an atrial depolarization and a successive RV depolarization and an LV AVI measurement circuit 799 to measure an LV AVI being the time interval between the atrial depolarization and a successive LV depolarization. User interface 752 includes a pacing parameter input 758, which replaces pacing parameter input 658. Pacing parameter input 758 includes an RV AVD input 792 to allow entry and/or adjustment of an RV AVD for timing the delivery of an RV pacing pulse after an atrial depolarization and an LV AVD input 794 for timing the delivery of an LV pacing pulse after the atrial depolarization.

Figure 8:
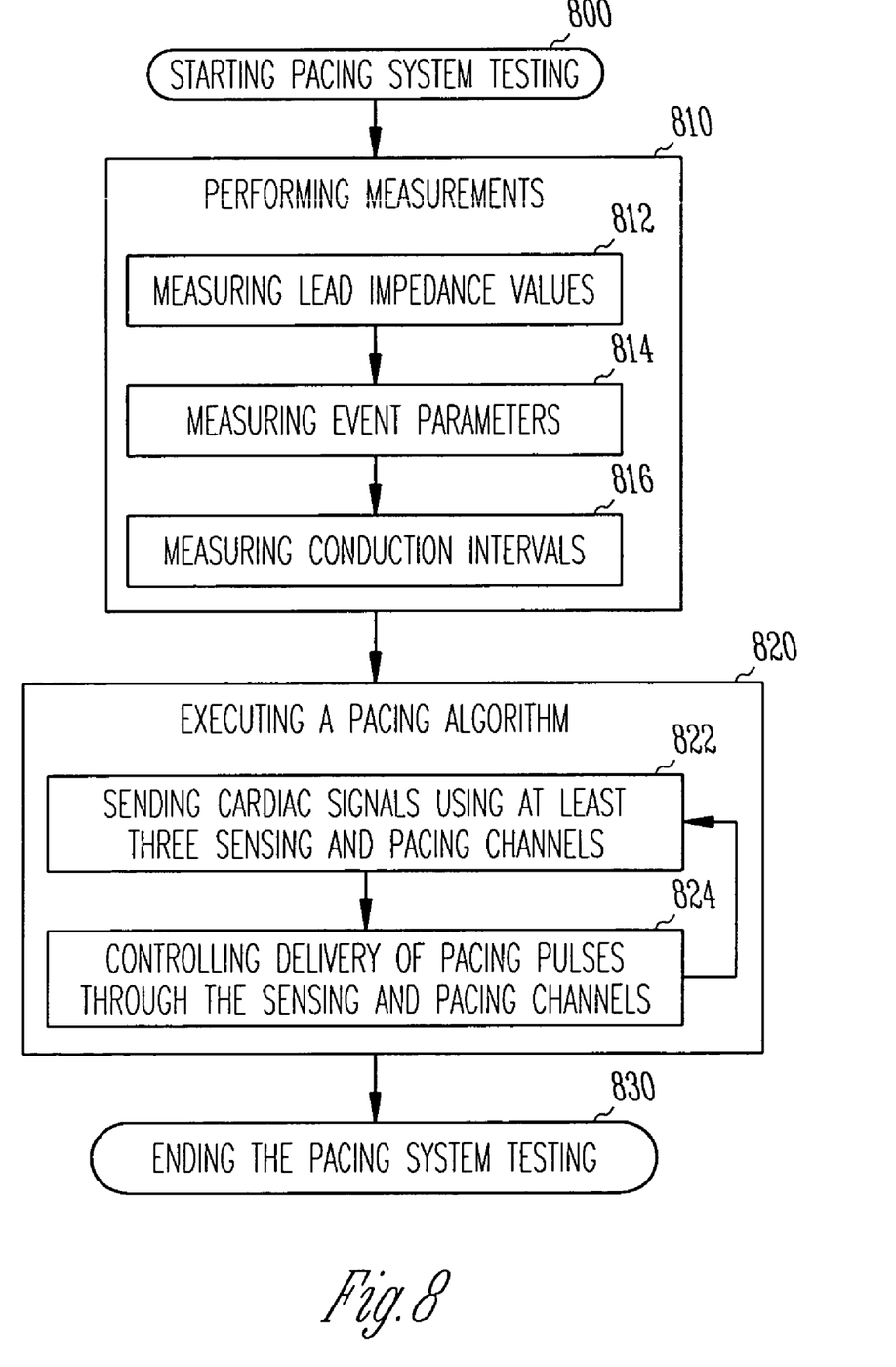
FIG. 8 is a flow chart illustrating an embodiment of a method for operating a PSA.

FIG. 8 is a flow chart illustrating an embodiment of a method for operating a PSA. The PSA has at least three individually controlled sensing and pacing channels each to be connected to a sensing-pacing lead. In one embodiment, the PSA includes PSA circuit 350 or 450.

A pacing system testing is started at 800, after the sensing and pacing channels are each connected to a sensing-pacing lead with one or more electrodes placed in or on a heart. In one embodiment, the pacing system testing is performed as part of the operation for implanting an implantable pacemaker into a patient. The pacing system testing includes performing measurements at 810 and executing a pacing algorithm to deliver pacing pulses at 820. Steps 810 and 820 are not necessarily performed in any particular order. Based on the objectives of the testing, such as predetermined as a pacing system testing protocol or determined by the user, steps 810 and 820, or portions thereof, are performed sequentially, concurrently, or iteratively.

Performing the measurements at 810 includes, but is not limited to, measuring lead impedance values at 812, measuring event parameters at 814, and measuring conduction intervals at 816. The lead impedance values are each associated with one of the sensing and pacing channels connected to the sensing-pacing lead. The event parameters are each associated with a cardiac event detected in one of the sensing and pacing channels. In one embodiment, the event parameters to be measured include the amplitude associated with the detected cardiac event. In a further embodiment, the event parameters to be measured include a slew rate associated the detected cardiac event. The conduction intervals are each a time interval between two cardiac events of different types. In one embodiment, the conduction intervals to be measured include time intervals each between a cardiac event detected in a sensing and pacing channel and a successive cardiac event detected in another sensing and pacing channel. Steps 812, 814, and 816 are not necessarily performed in accordance with any particular order or any other particular timing relationship. Based on the objectives of the testing, each of steps 812, 814, and 816 is performed continuously (such as on a beat-by-beat basis), periodically, or in response to a request by the user. In one embodiment, during at least a portion of the testing, steps 812, 814, and 816 are performed concurrently. The results of the measurement are displayed for viewing by the user.

To execute the pacing algorithm at 820, cardiac signals are sensed using at least three sensing and pacing channels at 822, and the delivery of pacing pulses through these sensing and pacing channels are controlled at 824. Specifically, a first cardiac signal indicative of first type cardiac events are sensed using a first sensing and pacing channel, a second cardiac signal indicative of second type cardiac events is sensed using a second sensing and pacing channel, and a third cardiac signal indicative of third type cardiac events are sensed using a third sensing and pacing channel. The delivery of the pacing pulses are controlled based on a plurality of pacing parameters and includes one or more of the delivery of pacing pulses using the first sensing and pacing channel, the delivery of pacing pulses using the second sensing and pacing channel, and the delivery of third pacing pulses using the third sensing and pacing channel. The plurality of pacing parameters includes user-programmable pacing parameters adjustable through a user interface of the PSA. The user-programmable pacing parameters include cross-channel pacing delays. In one embodiment, the first, second, and third type cardiac events are detected. Sense markers each indicative of a detection of one of the first, second, and third type cardiac events are produced, and pace markers each indicative of the delivery of a pacing pulse are produced. In one embodiment, the first, second, and third cardiac signals are displayed in real time. In a further embodiment, the sense and pace markers are displayed along with the first, second, and third cardiac signals. In another further embodiment, LEDs are used to present the sense and pace markers.

The pacing system testing ends at 830 when sensing-pacing leads are determined to be properly placed and a set of suitable pacing parameters are obtained. The sensing-pacing leads are disconnected from the PSA and connected to the implantable pacemaker. The implantable pacemaker is programmed using at least the set of suitable pacing parameters obtained during the pacing system testing.

Figure 9:
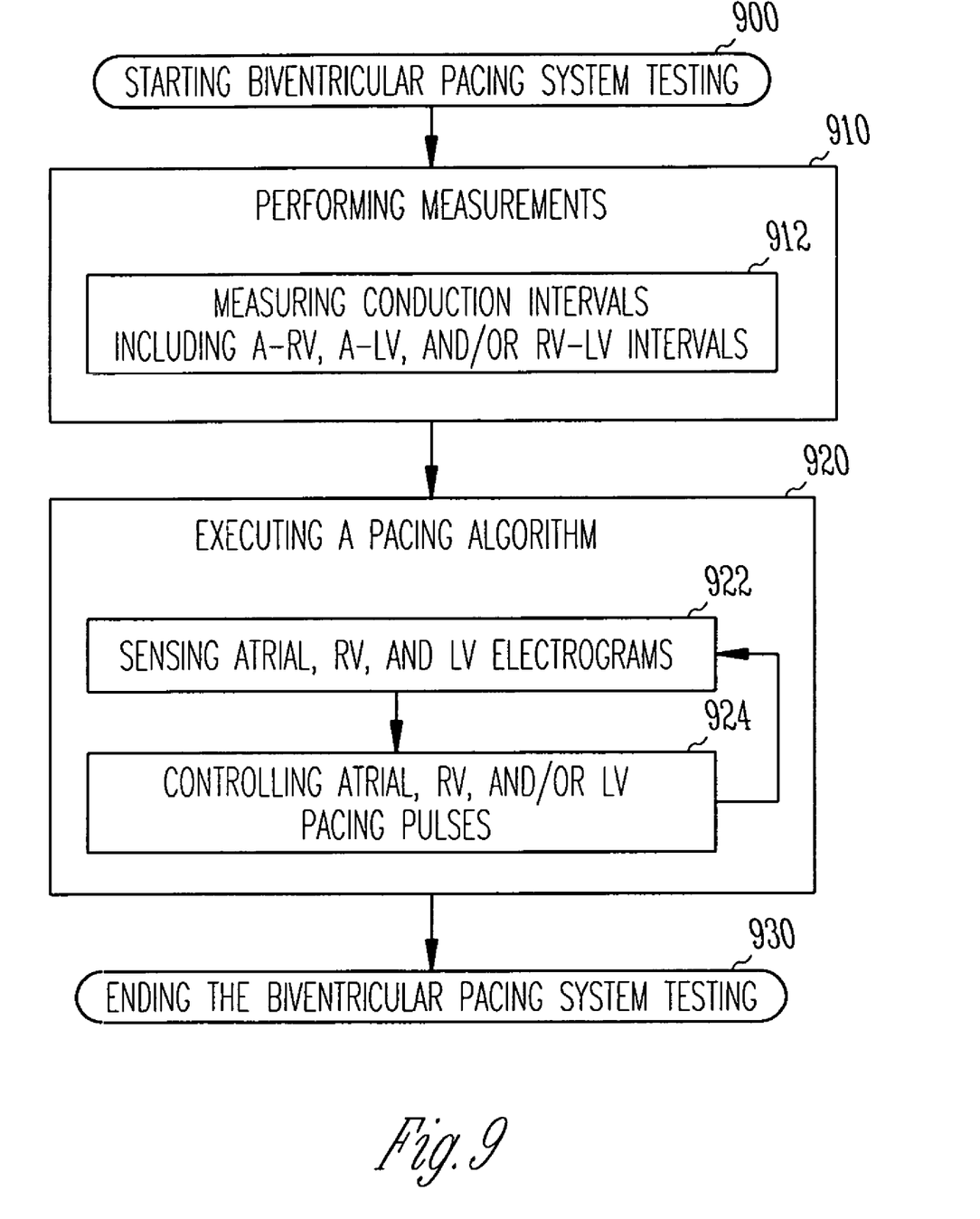
FIG. 9 is a flow chart illustrating an embodiment of a method for operating a PSA having atrial, RV, and LV sensing and pacing channels.

FIG. 9 is a flow chart illustrating an embodiment of a method for operating a PSA having an atrial sensing and pacing channel to be connected to an atrial lead, an RV sensing and pacing channel to be connected to an RV lead, and an LV sensing and pacing channel to be connected to an LV lead. In one embodiment, the PSA includes PSA circuit 650 or 750. The atrial, RV, and LV leads are sensing-pacing leads each allow for sensing an electrogram and delivering pacing pulses.

A biventricular pacing system testing is started at 900, after the sensing and pacing channels are each connected to a corresponding sensing-pacing lead. In one embodiment, the biventricular pacing system testing is performed as part of the operation for implanting an implantable biventricular pacemaker into a patient. The biventricular pacing system testing includes performing measurements at 910 and executing a pacing algorithm to deliver pacing pulses at 920. Steps 910 and 920 are not necessarily performed in any particular order. Based on the objectives of the testing, such as predetermined as a pacing system testing protocol or determined by the user, steps 910 and 920 are performed sequentially, concurrently, or iteratively. In one embodiment, a CRT pacing algorithm is executed at 920.

Performing the measurements at 910 includes, but is not limited to, measuring conduction intervals at 912. In various embodiments, the measurements further include measurements of lead impedance values each associated with one of the atrial, RV, and LV sensing and pacing channels and measurements of event parameters each associated with an atrial, RV, or LV depolarization. The conduction intervals are each the time interval between two depolarizations of a different cardiac chamber. Measurement of the conduction intervals at 912 includes measuring an A-RV interval being the time interval between an atrial depolarization and a successive RV depolarization, measuring an A-LV interval being the time interval between an atrial depolarization and a successive LV depolarization, and measuring an RV-LV interval being the time interval between an RV depolarization and a successive LV depolarization. Based on the objectives of the testing, the conduction intervals are measured continuously (such as on a beat-by-beat basis), periodically, or in response to a request by the user. The measured conduction intervals are displayed for viewing by the user.

To execute the pacing algorithm at 920, atrial, RV, and LV electrograms are sensed at 922, and the delivery of atrial, RV, and/or LV pacing pulses are controlled at 924. Specifically, an atrial electrogram indicative of atrial depolarizations is sensed using the atrial sensing and pacing channel, an RV electrogram indicative of RV depolarizations is sensed using the RV sensing and pacing channel, and an LV electrogram indicative of LV depolarizations is sensed using the LV sensing and pacing channel. The delivery of the pacing pulses are controlled based on a plurality of pacing parameters and includes one or more of the delivery of atrial pacing pulses using the atrial sensing and pacing channel, the delivery of RV pacing pulses using the RV sensing and pacing channel, and the delivery of LV pacing pulses using the LV sensing and pacing channel. The plurality of pacing parameters includes user-programmable pacing parameters that are adjustable through a user interface of the PSA. The user-programmable pacing parameters include atrioventricular and interventricular pacing delays. In one embodiment, the atrial, RV, and LV depolarizations are detected. Sense markers are produced to indicate the detection of each atrial, RV, or LV depolarization. Pace markers are each produced to indicate the delivery of an atrial, RV, or LV pacing pulse. In one embodiment, the atrial, RV, and LV electrograms are displayed in real time. In a further embodiment, the sense and pace markers are displayed along with the atrial, RV, and LV electrograms. In another further embodiment, six LEDs are used to present an atrial sense marker, an RV sense marker, an LV sense marker, an atrial pace marker, an RV pace marker, and an LV pace marker.

The pacing system testing ends at 930 when the atrial, RV, and LV leads are determined to be properly placed and a set of suitable pacing parameters are obtained. The atrial, RV, and LV leads are disconnected from the PSA and connected to the implantable biventricular pacemaker. The implantable biventricular pacemaker is programmed using at least the set of suitable pacing parameters obtained during the pacing system testing.

Figure 10:
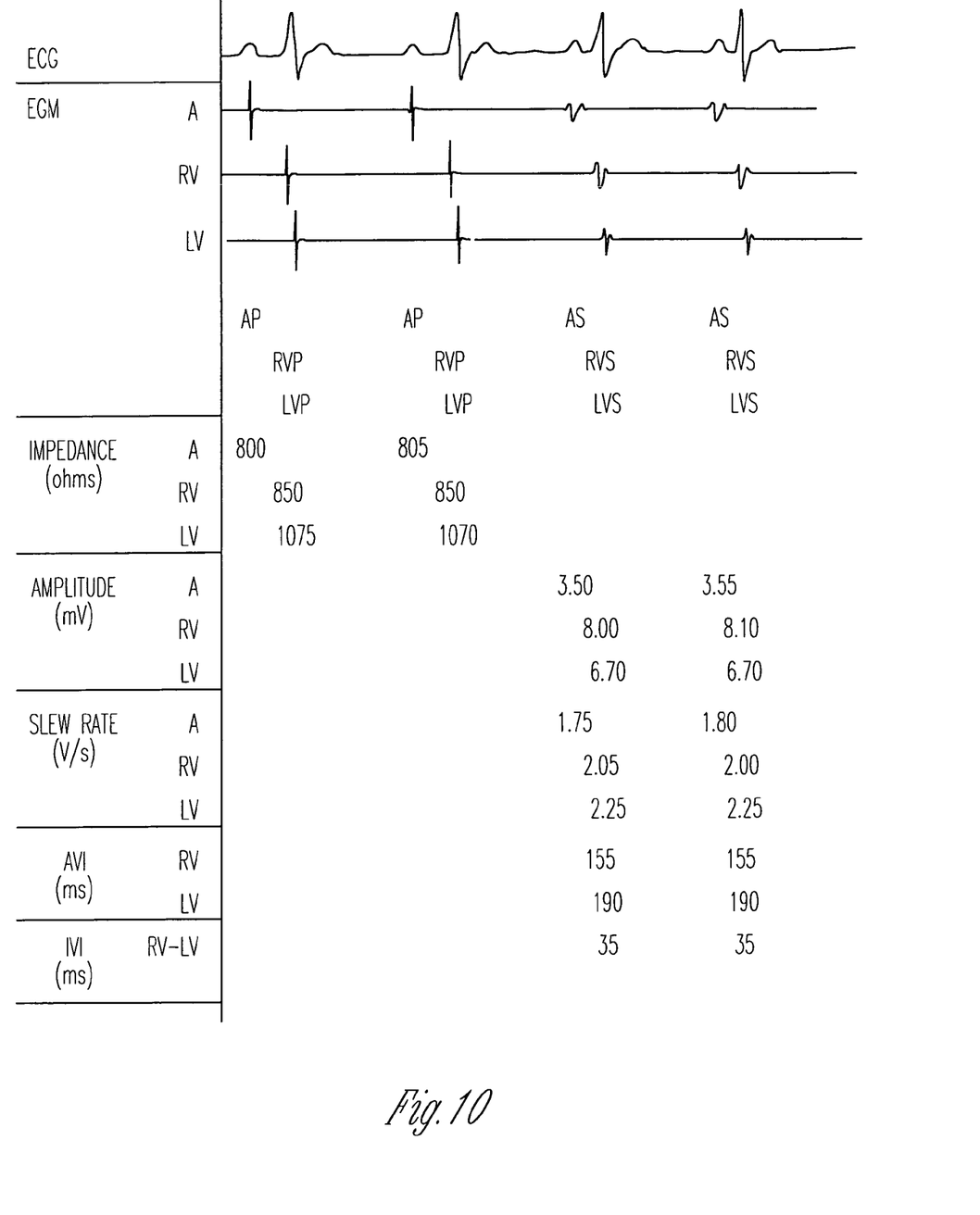
FIG. 10 is an illustration of an embodiment of portions of a display screen of the PSA.

FIG. 10 is an illustration of an embodiment of portions of display screen 666. Display screen 666 visually presents one or more of cardiac signals, event markers, and measurement markers. Examples of such cardiac signals, event markers, and measurement markers are illustrated in FIG. 10. The illustrated examples of the cardiac signals include surface ECG (ECG) and atrial (A), RV, and LV electrograms (EGMs). The illustrated examples of event markers include atrial (A) sense marker (AS), RV sense marker (RVS), LV sense marker (LVS), atrial (A) pace marker (AP), RV pace marker (RVP), and LV pace marker (LVP). The illustrated examples of measurement markers include atrial (A), RV, and LV impedance markers each displayed as a number in ohms, atrial (A), RV, and LV amplitude markers each displayed as a number in millivolts (mV), atrial (A), RV, and LV slew rate markers each displayed as a number in volts per second (V/s), RV and LV AVI markers each displayed as a number in milliseconds (ms), and IVI displayed as a number in milliseconds (ms). In various embodiments, display screen 666 visually presents one or more of cardiac signals, event markers, and measurement markers selected from signals and markers including, but not limited to these illustrated examples. In a specific embodiment, as illustrated in FIG. 10, display screen 666 visually presents cardiac signals, event markers, and measurement markers including all the illustrated examples. In various embodiments, display screen 666 visually presents cardiac signals, event markers, and measurement markers selected by a user of the PSA from available signals and markers such as the illustrated examples. Each displayed event marker or measurement marker is aligned with an associated cardiac event as seen on the ECG and/or one of the electrograms, or shown in another way to be visually perceived as related to the associated cardiac event.

In various embodiments, the measurement markers are displayed to present all or selected measurement results. Each measurement marker is displayed with a cardiac event following a measurement related to that cardiac event. Each impedance marker is displayed after the delivery of a pacing pulse with which a lead impedance is measured. The impedance marker is displayed as the value of the measured impedance in ohms. Each amplitude marker is displayed after a detected depolarization for which the amplitude of the electrogram is measured. The amplitude marker is displayed as the measured amplitude in millivolts. Each slew rate marker is displayed after a detected depolarization for which the slew rate of the electrogram is measured. The slew rate marker is displayed as the measured slew rate in volts per second. Each AVI marker is displayed after a detected RV or LV depolarization for which the AVI is measured. The AVI marker is displayed as the measured AVI in milliseconds. Each IVI marker is displayed after a detected RV or LV depolarization for which the IVI is measured. The IVI marker is displayed as the measured IVI in milliseconds.

It is to be understood that the above detailed description is intended to be illustrative, and not restrictive. For example, while a PSA is specifically discussed in the description above, the present subject matter is generally applicable to various types of external pacemakers or other device used for testing, evaluation, or analysis of pacing therapies. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A pacing system analyzer for use with at least first, second, and third electrodes placed in a heart and a computer-based medical device programmer, the pacing system analyzer comprising:
   a first sensing and pacing channel including a first sensing circuit adapted to sense a first cardiac signal indicative of first cardiac events through at least the first electrode and a first pacing circuit adapted to deliver first pacing pulses through at least the first electrode;
   a second sensing and pacing channel including a second sensing circuit adapted to sense a second cardiac signal indicative of second cardiac events through at least the second electrode and a second pacing circuit adapted to deliver second pacing pulses through at least the second electrode;

a third sensing and pacing channel including a third sensing circuit adapted to sense a third cardiac signal indicative of third cardiac events through at least the third electrode and a third pacing circuit adapted to deliver third pacing pulses through at least the third electrode;

a pacing control circuit coupled to the first, second, and third sensing and pacing circuit, the pacing control circuit adapted to control the delivery of one or more of the first, second and third pacing pulses using a plurality of pacing parameters including user-programmable pacing parameters;

a housing adapted to enclose the first, second, and third sensing and pacing channels and the pacing control circuit, the housing configured to be detachably inserted to the computer-based medical device programmer and electrically connected to the computer-based medical device programmer during operation of the pacing system analyzer; and a user interface being a user interface of the computer-based medical device programmer and electrically wired to the pacing control circuit, the user interface including:
a pacing parameter input adapted to allow programming of the user-programmable pacing parameters; and
a presentation device including a display screen adapted to display the first, second, and third cardiac signals in real time.

2. The pacing system analyzer of claim 1, further comprising a conduction interval measurement circuit, coupled to the first, second and third sensing and pacing channels and enclosed in the housing, to measure one or more conduction intervals each being a time interval between two cardiac events selected from the first, second, and third cardiac events.

3. The pacing system analyzer of claim 2, wherein the conduction interval measurement circuit comprises at least two of:
a first conduction interval measurement circuit to measure a first conduction interval being a time interval between one of the first cardiac events and one of the second cardiac events;
a second conduction interval measurement circuit to measure a second conduction interval being a time interval between one of the first cardiac events and one of the third cardiac events; and
a third conduction interval measurement circuit to measure a third conduction interval being a time interval between one of the second cardiac events and one of the third cardiac events.

4. The pacing system analyzer of claim 3, wherein the display screen is adapted to display one or more intervals of the first, second, and third conduction intervals in addition to the first, second, and third cardiac signals.

5. The pacing system analyzer of claim 3, wherein the pacing parameter input comprises at least two of:
a first cross-channel pacing delay input adapted to allow adjustment of a first cross-channel pacing delay being a pacing delay interval between the first sensing and pacing channel and the second sensing and pacing channel;
a second cross-channel pacing delay input adapted to allow adjustment of a second cross-channel pacing delay being a pacing delay interval between the first sensing and pacing channel and the third sensing and pacing channel; and
a third cross-channel pacing delay input adapted to allow adjustment of a third cross-channel pacing delay being a pacing delay interval between the second sensing and pacing channel and the third sensing and pacing channel.

6. The pacing system analyzer of claim 1, further comprising a lead impedance measurement circuit, coupled to the first, second and third sensing and pacing channels, to measure one or more lead impedance values each associated with one of the first, second and third sensing and pacing channels.

7. The pacing system analyzer of claim 6, wherein the display screen is adapted to display the one or more lead impedance values in addition to the first, second, and third cardiac signals.

8. The pacing system analyzer of claim 1, further comprising a cardiac event measurement circuit, coupled to the first, second and third sensing and pacing channels and enclosed in the housing, to measure one or more event parameters each associated with one of the first, second, and third cardiac events.

9. The pacing system analyzer of claim 8, wherein the cardiac event measurement circuit comprises an amplitude measurement circuit to measure one or more amplitudes each associated with the one of the first, second, and third cardiac events.

10. The pacing system analyzer of claim 9, wherein the cardiac event measurement circuit further comprises a slew rate measurement circuit to measure one or more slew rates each associated with the one of the first, second, and third cardiac events.

11. The pacing system analyzer of claim 10, wherein the display screen is adapted to display one or more of the one or more amplitudes and the one or more slew rates in addition to the first, second, and third cardiac signals.

12. The pacing system analyzer of claim 1, further comprising:
a cardiac event detection circuit, coupled to the first, second and third sensing and pacing channels and enclosed in the housing, to detect the first, second, and third cardiac events; and
an event marker generator, coupled to the cardiac event detection circuit and the pacing control circuit, to produce sense markers each indicative of a detection of one cardiac event of the first, second, and third cardiac events and pace markers each indicative of a delivery of one pacing pulse of the first, second, and third pacing pulses,
and wherein the display screen is adapted to display the sense markers and the pace markers along with the first, second, and third cardiac signals.

13. The pacing system analyzer of claim 12, wherein the presentation devices further comprises a plurality of light-emitting diodes indicative of the first, second, and third cardiac events and the first, second, and third pacing pulses.

14. The pacing system analyzer of claim 1, further comprising a surface electrocardiogram (ECG) sensing circuit to sense one or more surface ECG signals, and wherein the display screen is adapted to display the one or more surface ECG signals with the first, second, and third cardiac signals.

15. A pacing system analyzer for use with at least a first electrode placed in a right atrium of a heart, a second electrode placed in a right ventricle of the heart, and a third electrode placed in a left ventricle of the heart and a computer-based medical device programmer, the pacing system analyzer comprising:
an atrial sensing and pacing channel including an atrial sensing circuit adapted to sense an atrial electrogram indicative of atrial depolarizations through at least the first electrode and an atrial pacing circuit adapted to deliver atrial pacing pulses through at least the first electrode;

a right ventricular (RV) sensing and pacing channel including an RV sensing circuit adapted to sense an RV electrogram indicative of RV depolarizations through at least the second electrode and an RV pacing circuit adapted to deliver RV pacing pulses through at least the second electrode;

a left ventricular (LV) sensing and pacing channel including an LV sensing circuit adapted to sense an LV electrogram indicative of LV depolarizations through at least the third electrode and an LV pacing circuit adapted to deliver LV pacing pulses through at least the third electrode;

a pacing control circuit to control the atrial pacing circuit, the RV pacing circuit, and LV pacing circuit using a plurality of pacing parameters including user-programmable pacing parameters, the pacing control circuit including a pacing algorithm execution module to control the delivery of one or more of the atrial, RV and LV pacing pulses by executing a predetermined biventricular pacing algorithm;

a housing adapted to enclose the atrial, RV, and LV sensing and pacing channels and the pacing control circuit, the housing configured to be detachably inserted to the computer-based medical device programmer and electrically connected to the computer-based medical device programmer during operation of the pacing system analyzer; and a user interface being a user interface of the computer-based medical device programmer and electrically wired to the pacing control circuit, the user interface including a pacing parameter input adapted to allow adjustment of the user-programmable pacing parameters, the pacing parameter input adapted to allow programming of an interventricular delay being an offset interval between a delivery of one of the RV pacing pulses and a delivery of one of the LV pacing pulses.

16. The pacing system analyzer of claim 15, wherein the pacing algorithm execution module comprises a cardiac resynchronization therapy pacing algorithm execution module to executing a cardiac resynchronization therapy pacing algorithm.

17. The pacing system analyzer of claim 16, wherein the pacing parameter input comprises an atrioventricular delay input adapted to allow adjustment of an atrioventricular delay for timing the delivery of the RV or LV pacing pulses and an interventricular delay input adapted to allow adjustment of the interventricular delay.

18. The pacing system analyzer of claim 16, wherein the pacing parameter input comprises a first atrioventricular delay input adapted to allow adjustment of a first atrioventricular delay for timing a delivery of one of the RV pacing pulses after one of the atrial depolarizations and a second atrioventricular delay input adapted to allow adjustment of a second atrioventricular delay for timing a delivery of one of the LV pacing pulses after one of the atrial depolarizations.

19. The pacing system analyzer of claim 16, further comprising a conduction interval measurement circuit, coupled to the atrial, RV, and LV sensing and pacing channels and enclosed in the housing, to measure conduction intervals each being a time interval between two cardiac events selected from the atrial depolarizations, the RV depolarizations, and the LV depolarizations.

20. The pacing system analyzer of claim 19, wherein the conduction interval measurement circuit comprises:

a first atrioventricular interval measurement circuit to measure a first atrioventricular interval being a time interval between one of the atrial depolarizations and one of the RV depolarizations;

a second atrioventricular interval measurement circuit to measure a second atrioventricular interval being a time interval between one of the atrial depolarizations and one of the LV depolarizations; and an interventricular interval measurement circuit to measure an interventricular interval being a time interval between one of the RV depolarizations and one of the LV R-values.

21. The pacing system analyzer of claim 20, further comprising:

a depolarization detection circuit, coupled to the atrial, RV, and LV sensing and pacing channels and enclosed in the housing, to detect the atrial, RV, an LV depolarizations; and an event marker generator to produce sense markers each indicative of a detection of one of the atrial events, RV events, and LV events and pace markers each indicative of a delivery of a pacing pulse of the atrial, RV, and LV pacing pulses, and wherein the user interface comprises a display screen to display the atrial, RV, and LV electrograms in real time, along with the sense markers and the pace markers.

22. The pacing system analyzer of claim 21, further comprising a lead impedance measurement circuit, coupled to the atrial, RV, and LV sensing and pacing channels and enclosed in the housing, to measure lead impedance values each associated with one of the atrial, RV, and LV sensing and pacing channels.

23. The pacing system analyzer of claim 22, further comprising a depolarization parameter measurement circuit, coupled to the atrial, RV, and LV sensing and pacing channels and enclosed in the housing, to measure one or more depolarization parameters each associated with one of the atrial depolarizations, the RV depolarizations, and the LV depolarizations.

24. The pacing system analyzer of claim 23, wherein the user interface comprises a display screen adapted to display one or more of the atrial electrogram, the RV electrogram, the LV electrogram, the sense markers, the pace markers, the conduction intervals, the lead impedance values, and the one or more depolarization parameters.

25. The pacing system analyzer of claim 24, further comprising a surface electrocardiogram (ECG) sensing circuit to sense one or more surface ECG signals, and wherein the display screen is adapted to display one or more of the one or more surface ECG signals, the atrial electrogram, the RV electrogram, the LV electrogram, the sense markers, the pace markers, the conduction intervals, the lead impedance values, and the one or more depolarization parameters.

* * * * *